United States Patent [19]

Möller

[11] Patent Number: 5,736,864

[45] Date of Patent: Apr. 7, 1998

[54] APPARATUS FOR ASCERTAINING THE COMPLEX DIELECTRIC CONSTANT OF TOBACCO

[75] Inventor: Henning Möller, Hamburg, Germany

[73] Assignee: Hauni Maschinenbau AG, Hamburg, Germany

[21] Appl. No.: 670,519

[22] Filed: Jun. 27, 1996

[30] Foreign Application Priority Data

Jul. 14, 1995 [DE] Germany .................. 195 25 706.5

[51] Int. Cl.$^6$ ................................ G01R 27/26
[52] U.S. Cl. ................ 324/633; 324/636; 324/634
[58] Field of Search .................. 324/634, 636, 324/633, 637, 640, 639, 641

[56] References Cited

U.S. PATENT DOCUMENTS

| 4,651,085 | 3/1987 | Sakurai et al. | 324/636 |
| 4,875,494 | 10/1989 | Siems. | |
| 5,500,599 | 3/1996 | Stange | 324/634 |

FOREIGN PATENT DOCUMENTS

| 43 42 505 C1 | 4/1995 | Germany. | |
| 0245952 | 10/1987 | Japan | 324/634 |
| 1497531 | 7/1989 | U.S.S.R. | 324/634 |

*Primary Examiner*—Michael Brock
*Attorney, Agent, or Firm*—Darby & Darby

[57] ABSTRACT

The complex dielectric constant of successive increments of a stream of tobacco particles is indicative of the mass and/or moisture content of the tested increments. Instead of passing along two high-frequency resonators, as disclosed in German patent No. 43 42 505 to Stange, the stream is caused to pass through the inlets and outlets of the housings of two high-frequency resonators which are connected to a microwave generator and transmit high-frequency signals whose amplitudes are indicative of the complex dielectric constants. The signals from the two resonators are processed in a regulating unit wherein a circuit sums up the real and the imaginary parts of the complex dielectric constant.

11 Claims, 3 Drawing Sheets

APPARATUS FOR ASCERTAINING THE COMPLEX DIELECTRIC CONSTANT OF TOBACCO

BACKGROUND OF THE INVENTION

The invention relates to improvements in apparatus for ascertaining the complex dielectric constants of particulate materials which are contained in smokers' products, particularly tobacco and filter material for tobacco smoke (hereinafter referred to as tobacco). More particularly, the invention relates to improvements in apparatus for ascertaining the dielectric constant of tobacco by evaluating the detuning of a high-frequency resonator system, namely a detuning which is attributable to the presence of tobacco. Still more particularly, the invention relates to improvements in apparatus wherein at least one of two high-frequency resonators is provided with means for adjusting the resonance frequency and wherein a combined regulating or control and evaluating unit serves to regulate the operation of the resonators and/or the operation of a high-frequency sender in such a way that the two resonators are provided with high-frequency currents or fields of identical frequency which, in the absence of tobacco, is between the differently preselected or preadjusted resonance frequencies of the two resonators but, in the presence of tobacco, evaluates the amplitudes of high-frequency signals received in the two resonators and ascertains the complex dielectric constant of tobacco on the basis of the sum and difference values of such parameters of the high-frequency signals.

An apparatus of the above outlined character is disclosed in German patent No. 43 42 505 to Stange. The patented apparatus employs two resonators having housings each of which includes a first section surrounding with a conductive material at least one hemisphere of a solid-state resonator, and a second section which can be penetrated by electromagnetic alternating fields. The two high-frequency resonators can be positioned relative to each other in such a way that their conductive housing sections shield each other against mutual influencing and that their other housing sections, which are permeable to electromagnetic fields, confront the material to be tested. This means that only stray fields can penetrate outwardly into the tested material, such as tobacco. A drawback of the patented proposal is that the sensitivity and accuracy of the apparatus are unsatisfactory when the apparatus is put to use to ascertain the complex dielectric constant of a small and rapidly advancing commodity to be tested, such as a stream, filler, flow or rod of particulate material of the tobacco processing industry, for example, tobacco in a cigarette rod.

A cigarette rod which is ready to be subdivided into plain cigarettes of unit length or multiple unit length contains a rod-like filler of tobacco particles and a tubular wrapper consisting of cigarette paper and surrounding the filler. The overlapping marginal portions of the wrapper are bonded to each other and form a seam extending in the longitudinal direction of the cigarette rod. It is desirable that the mass flow of tobacco (namely the mass of tobacco per unit length) constituting the rod-like filler of the cigarette rod be at least substantially constant, at least in the major part of the running cigarette rod. The mass flow of tobacco must be ascertained in order to facilitate proper regulation of the extent to which the wrapper of the cigarette rod is filled with tobacco particles. At the present time, the mass flow is ascertained by resorting to radiation (such as beta rays or infrared radiation) which is weakened during penetration through a moving rod- or stream-like body of tobacco particles. The extent of weakening of radiation as a result of penetration through tobacco is indicative of the mass of tobacco at the testing station. It is also known to monitor the mass of tobacco particles in an advancing stream or rod by resorting to high-frequency testing apparatus. The signals which are obtained in a standard apparatus operating with beta rays or infrared radiation or high-frequency and are indicative of the mass of tobacco in successively tested increments of a cigarette rod are utilized to regulate the quantity of tobacco in the filler (prior to draping of the filler into a web of cigarette paper or other suitable wrapping material) in such a way that the mass flow of tobacco particles is at least substantially constant. In many instances, the thus obtained signals are utilized to change the position of a so-called trimmer or equalizer which serves to remove the surplus from successive increments of a continuously advancing tobacco stream in order to convert the stream into a rod-like filler which is ready for draping into a web of cigarette paper or the like. Reference may be had, for example, to U.S. Pat. No. 4,875,494 which discloses an apparatus for the making of a continuous cigarette rod.

OBJECTS OF THE INVENTION

An object of the invention is to provide an apparatus which can be utilized to ascertain the complex dielectric constant of tobacco and constitutes an improvement over and a further development of apparatus disclosed in German patent No. 43 42 505 to Stange.

Another object of the invention is to provide an apparatus which can ascertain the complex dielectric constant of a continuous stream or flow of tobacco particles advancing at a speed which is required in a modern high-speed cigarette making machine.

A further object of the invention is to provide novel and improved high-frequency resonators for use in the above outlined apparatus.

An additional object of the invention is to provide novel and improved resonator housings for use in the above outlined apparatus.

Still other object of the invention is to provide a tobacco rod or filter rod making machine which embodies, or which is combined with, an apparatus of the above outlined character.

A further object of the invention is to provide a novel and improved method of ascertaining the complex dielectric constant of tobacco in an apparatus which employs high-frequency resonators.

Another object of the invention is to provide a highly sensitive and highly accurate apparatus for ascertaining the complex dielectric constant of tobacco.

SUMMARY OF THE INVENTION

The invention is embodied in an apparatus for ascertaining or determining the complex dielectric constant of a flow of smokable material which is advanced along a predetermined path. The improved apparatus comprises a resonator assembly including first and second high-frequency resonators which respectively have first and second housings surrounding first and second portions of the predetermined path. In accordance with a feature of the invention, each of the housings has an inlet and an outlet for the flow of smokable material in the respective portion of the path. At least one of the first and second resonators is a variable-frequency resonator and includes means for varying its resonance frequency. The apparatus further comprises a signal-evaluating regulating or control unit for at least one of (a) the resonators and (b) a high-frequency sender. The regulating or control unit includes means for applying to the resonators high-frequency currents or fields having a first frequency, and the first and second resonators have different second and third resonance frequencies in the absence of smokable material in the aforementioned portions of the predetermined path. The first frequency is between the second and third frequencies, and the assembly including the first and second resonators is detuned when the aforementioned portions of the predetermined path contain smokable material. The regulating or control unit includes means for ascertaining the complex dielectric constant of smokable material in the aforementioned portions of the predetermined path, and such complex dielectric constant is or can be indicative of the mass and/or moisture content of the tested smokable material. The complex dielectric constant is ascertained on the basis of the determination of amplitudes of first and second high-frequency signals which are respectively received by the first and second resonators and on the basis of a processing of the sums of and the differences between such parameters of the first and second signals.

The flow of smokable material can constitute the rod-like filler of a cigarette rod, and the smokable material can include or constitute natural tobacco, reconstituted tobacco and/or artificial tobacco and/or filter material for tobacco smoke. Furthermore, the aforementioned filler can contain smokable material in a wrapper which, together with the filler, constitutes a cigar rod or a cigarillo rod.

The aforementioned first frequency is or can be at least substantially midway between the second and third frequencies in the absence of smokable material in the aforementioned portions of the predetermined path.

At least one of the housings can constitute an at least substantially symmetrical housing, and the sender can include conductor means (e.g., coaxial cables) for the application of high-frequency currents or fields to the resonators, and the apparatus can further comprise second conductor means (e.g., coaxial cables) for the transmission of high-frequency signals from the resonators to the regulating or control unit.

The housing of at least one of the resonators can constitute a rotationally symmetrical housing (e.g., a cylinder), and the centers of the inlet and the outlet of such rotationally symmetrical housing can be located on the axis of the housing.

The apparatus can further comprise an additional resonator in at least one of the housings. Such additional resonator can constitute a solid-state resonator and is or can be provided with an opening for the flow of smokable material from the inlet to the outlet of the respective housing.

Tubular guide means can be provided for the flow of smokable material in the aforementioned portions of the predetermined path, and such apparatus can further comprise preferably tubular shields of electrically conductive material (e.g., shields consisting of or at least containing a metallic material) which at least partially surround the guide means at the inlet(s) and/or at the outlet(s) of the housing(s). Such tubular guide means and the shields can be provided irrespective of whether or not at least one of the housings confines an additional resonator.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawings.

DESCRIPTION OF PREFERRED EMBODIMENTS

Figure 1:
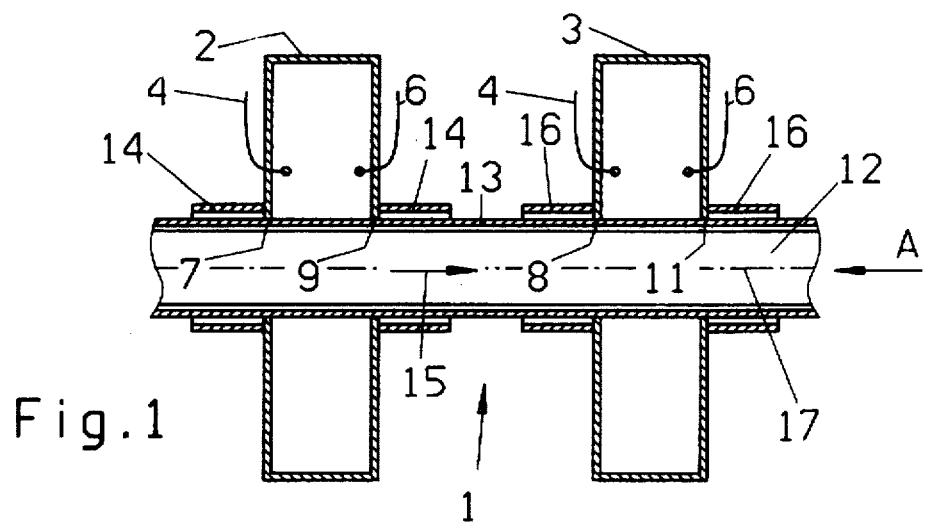
FIG. 1 is a schematic axial sectional view of an apparatus which embodies one form of the invention and comprises two coaxial high-frequency resonators connectable with a source of microwaves.
Figure 2:
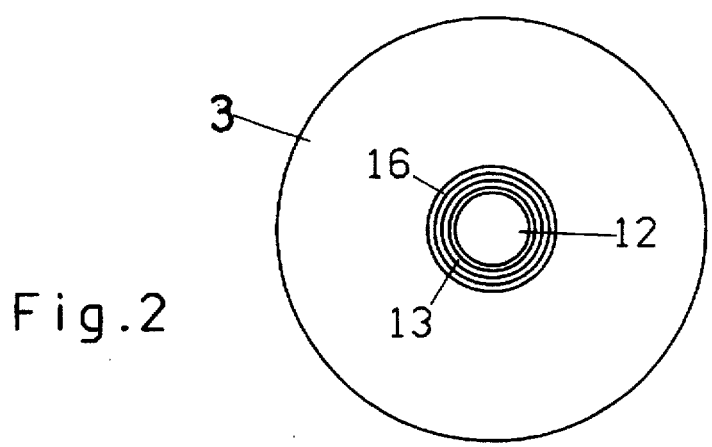
FIG. 2 is an end elevational view substantially as seen in the direction of the arrow A in FIG. 1.

Referring first to FIGS. 1 and 2, there is shown an apparatus which comprises an assembly 1 of two high-frequency resonators 2 and 3 having rotationally symmetrical (e.g., cylindrical) housings made of an electrically conductive material, e.g., copper. It is within the purview of the invention to replace the illustrated cylindrical resonator housings with other rotationally symmetrical housings (e.g., conical housings) or with housings having a polygonal cross-sectional outline. The reference numerals 4 and 6 denote conductors (e.g., coaxial cables) the first of which serve to establish in the housings of the resonators 2, 3 high-frequency electromagnetic fields (microwaves), and the second of which serve to decouple the high-frequency fields. The conductors 4, 6 are or can be provided with customary coupling loops or probes, not shown.

The housing of at least one of the resonators 2 and 3 can be provided with suitable means for selection and/or adjustment of resonance or oscillation frequency. For example, such frequency adjusting and/or selecting means can include at least one standard screw for each of the two housings.

The method which can be practiced with the apparatus including the 1 of FIGS. 1 and 2 in order to ascertain the complex dielectric constant of tobacco is fully disclosed in the aforementioned German patent No. 43 42 505 to Stange to which reference may be had, if necessary, and which is incorporated herein by reference. Thus, the complex dielectric constant $\Delta \epsilon$ can be ascertained on the basis of the following final equations:

$$\Delta \epsilon \propto \frac{F1 - F2}{F10 + F20}$$

wherein $\Delta \epsilon'$ constitutes the real part of the complex dielectric constant and wherein $\Delta$ denotes the difference (a) between the housings of the resonators 2, 3 while the housings are being traversed by a tobacco stream 12 and (b) the empty housings, and $$\Delta\epsilon'' \propto \frac{F10 + F20 - (F1 + F2)}{F10 + F20}$$

wherein $\Delta\epsilon''$ constitutes the imaginary part of the complex dielectric constant and wherein $\Delta$ again denotes the aforediscussed difference between the housings of the resonators 2, 3 (a) while the housings are being traversed by the tobacco stream 12 and (b) the empty housings.

Since the atmospheric air, which fills the housings of the resonators 2 and 3 when such housings do not confine portions of a tobacco stream, has a dielectric constant approximating 1, $\Delta\epsilon'$ and $\Delta\epsilon''$ reasonably accurately reflect the values of $\epsilon'$ and $\epsilon''$, respectively.

Figure 3:
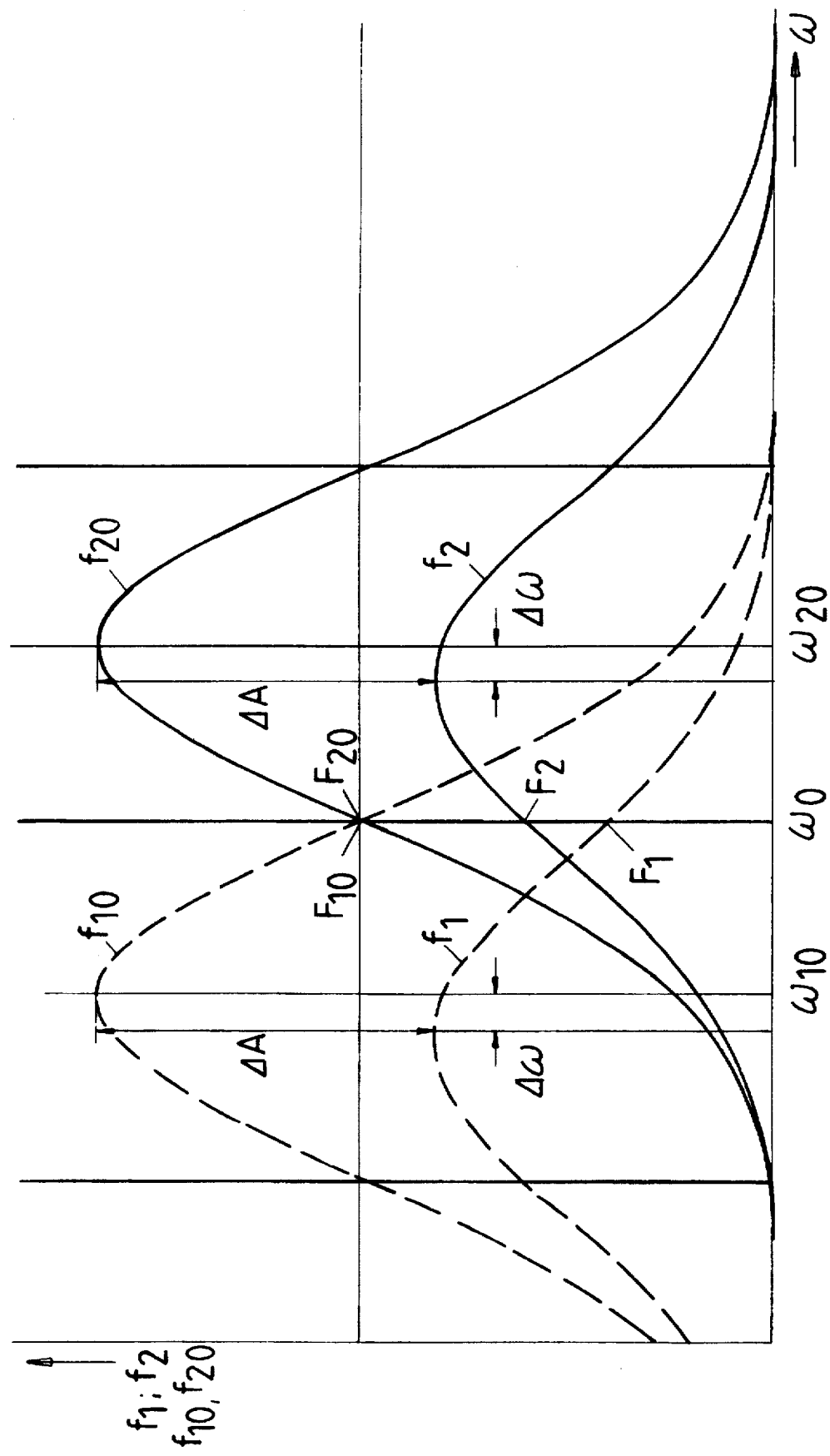
FIG. 3 is a diagram with a first set of resonance curves denoting the conditions prevailing when the housings of the resonators are traversed by a tobacco stream and a second set of resonance curves denoting the conditions prevailing in the absence of a tobacco stream.

The values of F1, F2, F10 and F20 can be ascertained on the basis of resonance curves f10, f20 (when the housings of the resonators 2 and 3 are empty) and f1, f2 (when the housings are being traversed by a tobacco stream). As can be seen in the diagram of FIG. 3, the resonance curves are formed in such a way that the (second and third) resonance frequencies $\omega 10$ and $\omega 20$ in the housings of the resonators 2 and 3 are, respectively, slightly below and slightly above an operational (first) frequency $\omega_0$ of microwaves which are being applied to the two housings. When the housings of the resonators 2, 3 contain portions of a flow of smokable material, the resonance frequencies of both resonance curves are shifted in directions toward lower frequencies by a value $\Delta\omega$. In addition, the amplitudes of the resonance frequencies drop due to damping of the microwaves by the advancing material (such as tobacco) by a value $\Delta A$. When the housings of the resonators 2 and 3 are empty, the values F10 and F20 (e.g., the voltages of rectified microwaves which are taken off the coaxial conductors (such as coaxial cables) 6) are identical if the operational frequency $\omega$ is the same and if the housings of the resonators 2, 3 are identical. The value F1 is ascertained, for example, as the voltage of rectified microwaves at the coaxial conductor or cable 6 of the housing of the resonator 2 while the housing contains tobacco. The value F2 is ascertained, for example, as voltage of the rectified microwaves at the coaxial conductor or cable 6 of the housing of the resonator 3 while such housing contains tobacco.

Figure 4:
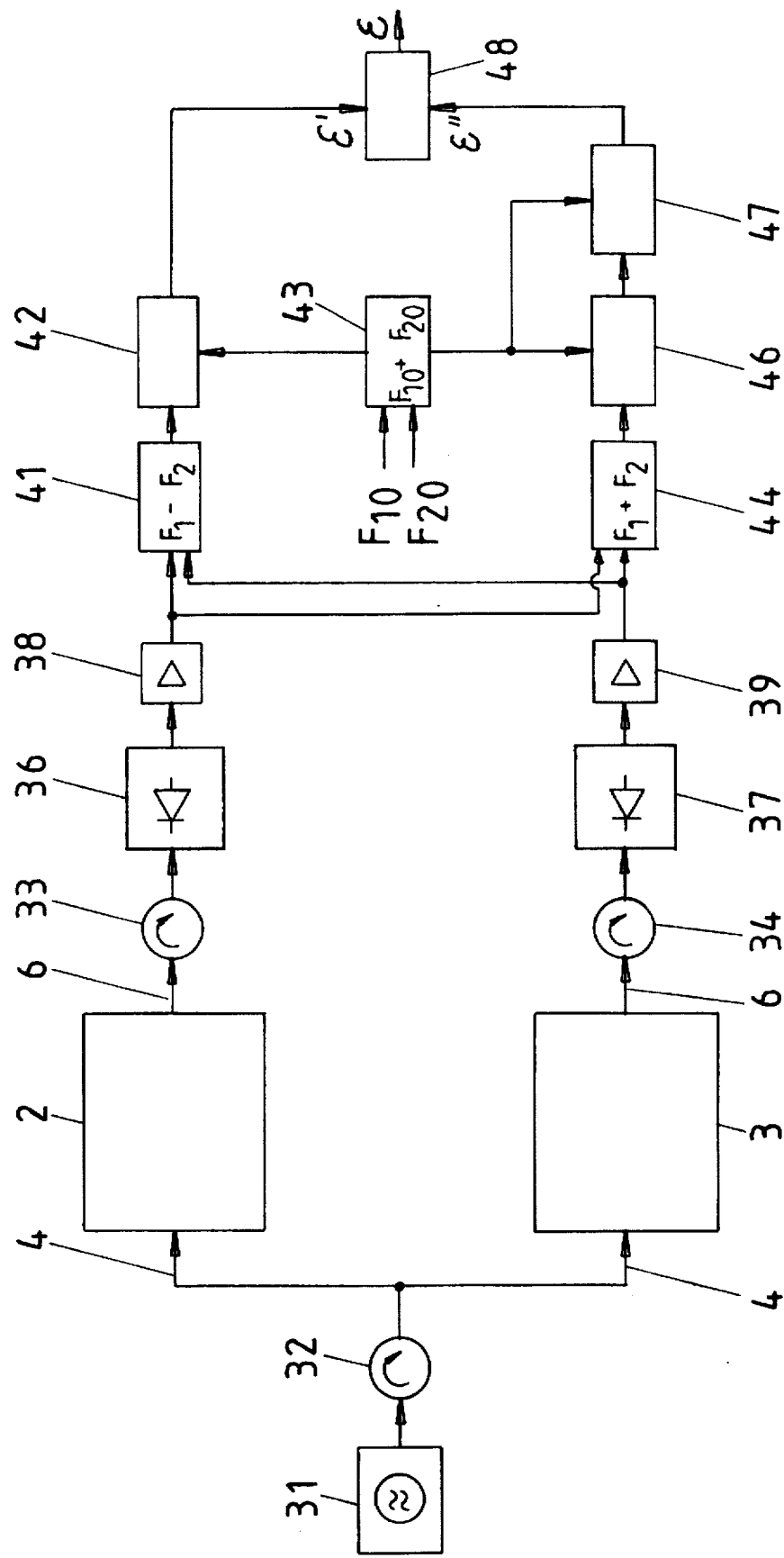
FIG. 4 is a diagrammatic view of a control or regulating unit which can be resorted to in order to ascertain the real and imaginary components of the complex dielectric constant of the material being tested during advancement through the housings of the two resonators.

The determination of the values of $\epsilon'$ and $\epsilon''$, which upon complex addition, furnish the value $\epsilon$, will be described with reference to the diagram of FIG. 4.

A microwave generator or sender 31 transmits, by way of a standard feedback-preventing microwave circulator 32, high-frequency microwaves (preferably in the gigahertz range, e.g., approximately 6 gigahertz) to the coaxial conductors or cables 4 for the housings of the resonators 2 and 3. The output signals are influenced by the material (tobacco) in the housings and are transmitted to microwave diodes 36 and 37 by way of microwave circulators 33, 34, respectively. For example, the microwave diodes 36, 36 can be those known as Type HP 847 2B obtainable from Hewlett-Packard, D-71034 Böblingen, Federal Republic Germany, and their function is to transform the high-frequency microwaves into direct-current voltage signals corresponding to F1 and F2, respectively. The direct-current voltage signal from the housing of the resonator 2 is amplified by an amplifier 38, and the direct-current voltage signal from the housing of the resonator 3 is amplified by an amplifier 39. The thus amplified signals are transmitted to a differentiating circuit 41 which furnishes a signal denoting the value of F1–F2. The signal at the output of the circuit 41 is transmitted to a dividing stage 42 which also receives a signal from the output of a summing circuit 43. The signal at the output of the circuit 43 denotes the sum of the constant signals F10 and F20. The signal at the output of the dividing stage 42 is the dividend of signals transmitted by the circuits 41 and 43 and is indicative of the real portion $\epsilon'$ of the complex dielectric constant $\epsilon$ of the tested material (such as tobacco).

A summing circuit 44 processes the signals from the outputs of the amplifiers 38 and 39 into a sum signal which is transmitted to a subtracting circuit 46 wherein such signal is subtracted from the signal transmitted by the summing circuit 43. The signal which is transmitted by the circuit 43 is further transmitted to one input of a dividing or quotient forming circuit 47 another input of which is connected with the output of the subtracting circuit 46. The signal at the output of the circuit 47 is a quotient of the signals transmitted by the circuits 43 and 46, and such quotient signal corresponds to the imaginary part $\epsilon''$ of the complex dielectric constant $\epsilon$, the latter being generated from $\epsilon'$ and $\epsilon''$ in a complex summing circuit 48. The electric signals which correspond to the above outlined relationships can be utilized to arrive at conclusions pertaining to the mass and/or the moisture content of tobacco in a flow of smokable material which passes through the housings of the resonators 2 and 3.

In order to permit a flow 12 to pass therethrough, the housing of the resonator 2 is provided with an inlet opening 7 and an outlet opening 9, and the housing of the resonator 3 is provided with an inlet opening 8 and an outlet opening 11. The flow 12 is caused to advance in a centrally located elongated tubular guide 13 which is made of an electrically non-conductive material, such as quartz. The direction of advancement of the flow 12 is indicated by the arrow 15. The guide 13 prevents particles of tobacco and/or dust and/or other solid contaminants from penetrating into the housings of the resonators 2 and 3 wherein such foreign particles could cause disturbances such as inaccurate determination of the complex dielectric constant.

FIG. 1 further shows tubular shields 14 and 16 which consist of a suitable electrically conductive material (such as metal) and serve to prevent undesirable issuance of the high-frequency field from the inlets and outlets of the housings of the radiators 2 and 3, respectively.

The feature that the common axis 17 of the housings of the radiators 2 and 3 coincides with the axis of the guide 13 and of the flow 12 in the guide 13 contributes to the symmetry of the apparatus 1 and to optimal test results. The centers of the inlets 7, 8 and outlets 9, 11 are preferably located on the axis 17.

Figure 5:
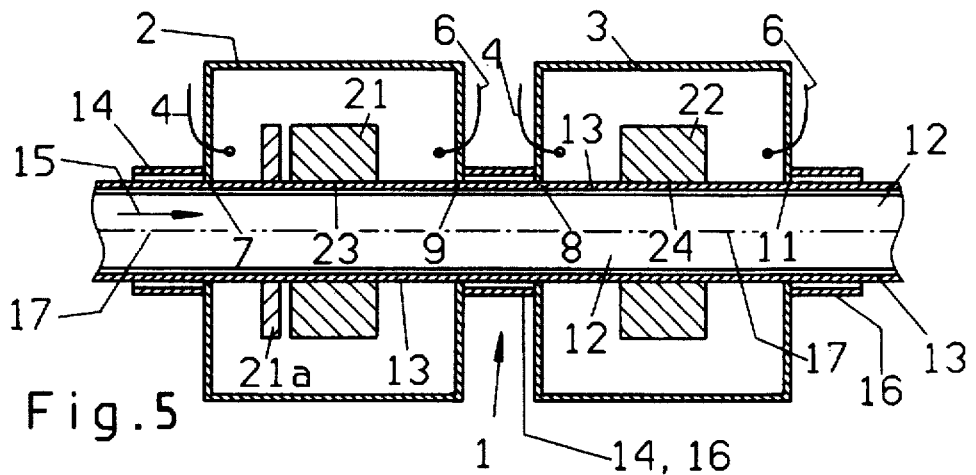
FIG. 5 is a schematic axial sectional view of a modified apparatus wherein an additional resonator is provided in the housing of each of two main or primary resonators corresponding to those shown in FIG. 1.

The apparatus which is shown in FIG. 5 differs from the apparatus of FIGS. 1 and 2 in that the housings of the main or primary resonators 2 and 3 contain additional or auxiliary dielectric resonators 21 and 22, respectively. For example, the additional resonators 21, 22 can be made of a suitable ceramic material and their positions in the housings of the respective primary resonators 2 and 3 are fixed by suitable distancing elements, not specifically shown in FIG. 5. The resonators 21 and 22 are respectively provided with central openings or passages 23, 24 for the tubular guide 13 which surrounds the advancing flow 12. The additional resonator 21 in the housing of the primary resonator 2 includes a first portion and a second portion 21a which is movable toward and away from the first portion in and counter to the direction indicated by the arrow 15; this renders it possible to ascertain the resonance or natural frequency. The additional resonator 22 can be replaced with a resonator which is identical with or analogous to the composite resonator 21.

An advantage of the apparatus which is shown in FIG. 5 is that its additional resonators 21 and 22 render it possible to enhance the sensitivity of the apparatus and the accuracy of measurements upon the flow 12.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art and, therefore, such adaptations should and are intended to be comprehended within the meaning and range of equivalence of the appended claims.

What is claimed is:

1. Apparatus for ascertaining the complex dielectric constant of a filler of a cigarette rod which is advanced along a predetermined path, comprising a resonator assembly including first and second high-frequency resonators respectively having first and second housings surrounding first and second portions of said path, at least one of said housings being an at least substantially rotationally symmetrical housing and each of said housings having an inlet and an outlet for the filler in the respective portion of said path, at least one of said resonators being a variable-frequency resonator and including means for varying the resonance frequency thereof; a high-frequency sender including first conductor means for the application of high-frequency fields to said resonators; a signal-evaluating regulating unit operatively connected with at least one of said resonators and said high-frequency sender; and second conductor means for the transmission of signals from said resonators to said regulating unit, said sender including means for applying to said resonators said high-frequency fields having a first frequency and said first and second resonators having different second and third resonance frequencies in the absence of a filler in said portions of said path, said first frequency being at least substantially midway between said second and third frequencies in the absence of a filler in said portions of said path, said resonator assembly being detuned when said portions of said path contain a filler and said regulating unit including means for ascertaining the complex dielectric constant of a filler in said portions of said path on the basis of a determination of amplitudes of first and second high-frequency signals respectively determined by said first and second resonators and transmitted to said regulating unit by said second conductor means, and on the basis of the processing of the sums of and differences between said first and second signals.

2. The apparatus of claim 1, wherein said rotationally symmetrical housing is a cylindrical housing.

3. The apparatus of claim 1, further comprising an additional resonator in at least one of said housings.

4. The apparatus of claim 3, wherein said additional resonator is a solid-state resonator.

5. The apparatus of claim 3, wherein said additional resonator has an opening for the filler between the inlet and the outlet of the respective housing.

6. The apparatus of claim 5, further comprising tubular guide means for the filler in said portions of said path.

7. The apparatus of claim 6, further comprising tubular shields of electrically conductive material surrounding said guide means at said inlets and said outlets.

8. The apparatus of claim 7, wherein said shields contain a metallic material.

9. The apparatus of claim 1, further comprising tubular guide means for the filler in said portions of said path.

10. The apparatus of claim 9, further comprising tubular shields of electrically conductive material surrounding said guide means at said inlets and said outlets.

11. The apparatus of claim 10, wherein said shields contain a metallic material.

* * * * *